(12) United States Patent
Kasagi et al.

(10) Patent No.: US 10,883,986 B2
(45) Date of Patent: Jan. 5, 2021

(54) KIT FOR QUANTITATIVELY DETERMINING BILE ACID IN BIOLOGICAL SAMPLE, AND METHOD FOR QUANTITATIVELY DETERMINING BILE ACID IN BIOLOGICAL SAMPLE

(71) Applicant: FUJIFILM Corporation, Tokyo (JP)

(72) Inventors: Noriyuki Kasagi, Kanagawa (JP); Hiroyuki Chiku, Kanagawa (JP); Ayumi Era, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/115,594

(22) Filed: Aug. 29, 2018

(65) Prior Publication Data

US 2018/0372737 A1  Dec. 27, 2018

Related U.S. Application Data

(63) Continuation of application No. PCT/JP2017/007746, filed on Feb. 28, 2017.

(30) Foreign Application Priority Data

Feb. 29, 2016 (JP) .................. 2016-037298

(51) Int. Cl.
*G01N 33/543* (2006.01)
*G01N 33/48* (2006.01)
*G01N 33/53* (2006.01)

(52) U.S. Cl.
CPC ....... *G01N 33/54393* (2013.01); *G01N 33/48* (2013.01); *G01N 33/53* (2013.01); *G01N 33/543* (2013.01); *G01N 33/54313* (2013.01)

(58) Field of Classification Search
CPC combination set(s) only.
See application file for complete search history.

(56) References Cited

U.S. PATENT DOCUMENTS

| | | | |
|---|---|---|---|
| 4,693,912 A * | 9/1987 | Spadaro | G01N 33/54313 427/213.3 |
| 5,631,138 A | 5/1997 | Kano et al. | |
| 6,171,801 B1 | 1/2001 | Staples et al. | |
| 6,887,669 B1 | 5/2005 | Staples et al. | |
| 2004/0096900 A1 | 5/2004 | Laurie et al. | |
| 2005/0191762 A1* | 9/2005 | Staples | G01N 33/94 436/518 |
| 2014/0342445 A1* | 11/2014 | Ingber | C12M 25/02 435/294.1 |
| 2015/0355175 A1 | 12/2015 | Fujiwara et al. | |

FOREIGN PATENT DOCUMENTS

| | | |
|---|---|---|
| CN | 102539791 | 7/2012 |
| EP | 0402062 | 12/1990 |
| EP | 0403271 | 12/1990 |
| EP | 0714028 | 5/1996 |
| EP | 2574927 | 4/2013 |
| GB | 2020014 | 11/1979 |
| JP | S54149700 | 11/1979 |
| JP | H03216553 | 9/1991 |
| JP | H08145995 | 6/1996 |
| JP | H11108933 | 4/1999 |
| JP | H11248702 | 9/1999 |
| JP | 2001513877 | 9/2001 |
| JP | 2004515763 | 5/2004 |
| JP | 2015230248 | 12/2015 |

OTHER PUBLICATIONS

"Search Report of Europe Counterpart Application", dated Dec. 10, 2018, p. 1-p. 5.
Toshiki Kamano, et al., "Diagnostic Significance of Measurement of Fecal Bile Acids in Colorectal Cancer Patients," Current Therapeutic Research, vol. 55, No. 8, Aug. 1, 1994, pp. 1-5.
Norihiro Kobayashi, et al., "A monoclonal antibody-based enzyme-linked immunosorbent assay of glycolithocholic acid sulfate in human urine for liver function test," Steroids, Elsevier Science Inc., vol. 67, No. 10, Sep. 1, 2002, pp. 1-7.
Rachel L. Seibert et al.,"Evaluation of a semiquantitative SNAP test for measurement of bile acids in dogs", Peer J, Aug. 26, 2014. e539,pp. 1-11.
Hiroyuki Chiku et al.,"Development of Quantitative Immunoassay Reagent " Fuji Dri-Chem Immuno Au Cartridge vc-TSH and v-COR ,Fujifilm Research & Development, vol. 60, Mar. 27, 2015, pp. 33-38.
"International Search Report (Form PCT/ISA/210)"of PCT/JP2017/007746, dated May 30, 2017, with English translation thereof, pp. 1-5.
"Written Opinion of the International Searching Authority (Form PCT/ISA/237)" of PCT/JP2017/007746, dated May 30, 2017, with English translation thereof, pp. 1-7.

(Continued)

*Primary Examiner* — Tracy Vivlemore
*Assistant Examiner* — Nam P Nguyen
(74) *Attorney, Agent, or Firm* — JCIPRNET

(57) ABSTRACT

An object of the present invention is to provide a kit for quantitatively determining a bile acid, in which it is possible to improve measurement accuracy by sufficiently dissociating the bile acid from a polymer component, and to rapidly carry out the quantitative determination of the bile acid with high accuracy under various environments, and a method for quantitatively determining the bile acid.

According to the present invention, a kit for quantitatively determining a bile acid in a biological sample, including a compound represented by General Formula (I) defined in the present specification in a dry state; a fluorescent particle that has a first binding substance capable of binding to the bile acid; and a substrate that has a detection region having a second binding substance capable of binding to any one of the bile acid and the first binding substance, is provided.

18 Claims, 2 Drawing Sheets

(56) References Cited

OTHER PUBLICATIONS

Masaru Matsumoto et al., "Development of an Enzyme-Linked Immunosorbent Assay for Fecal Bile Acid", Rinsho Byori, Nov. 30, 2004, pp. 891-896.
Yue Zhang et al., "Development of an Enzyme-Linked Immunosorbent Assay for Chenodeoxycholic Acid Using an Anti-Chenodeoxycholic Acid Monoclonal Antibody", Analytical Methods, Apr. 14, 2015, pp. 4583-4589.
Teru Kato et al., "Bioassay of Bile Acids Using an Enzyme-Linked DNA Aptamer", Analyst, Jul. 12, 2000, pp. 1371-1373.
"Office Action of China Counterpart Application", dated Aug. 14, 2020, with English translation thereof, pp. 1-21.

* cited by examiner

KIT FOR QUANTITATIVELY DETERMINING BILE ACID IN BIOLOGICAL SAMPLE, AND METHOD FOR QUANTITATIVELY DETERMINING BILE ACID IN BIOLOGICAL SAMPLE

CROSS-REFERENCE TO RELATED APPLICATIONS

This application is a Continuation of PCT International Application No. PCT/JP2017/007746 filed on Feb. 28, 2017, which claims priority under 35 U.S.C § 119(a) to Japanese Patent Application No. 2016-037298 filed on Feb. 29, 2016. Each of the above application(s) is hereby expressly incorporated by reference, in its entirety, into the present application.

BACKGROUND OF THE INVENTION

1. Field of the Invention

The present invention relates to a kit for quantitatively determining a bile acid in a biological sample, and a method for quantitatively determining a bile acid in a biological sample.

2. Description of the Related Art

A fluorescence detection method has been in wide use as a highly sensitive and simple measurement method for quantitatively determining proteins, enzymes, inorganic compounds, and the like. The fluorescence detection method is a method in which fluorescence emitted in a case where a sample considered to include a substance to be measured which is excited by light of a specific wavelength so as to emit fluorescence, is irradiated with excitation light of the specific wavelength, is detected, and thus the presence of the substance to be measured is confirmed. In a case where the substance to be measured is not a fluorescent substance, a substance that specifically binds to the substance to be measured is labeled with a fluorescent dye and brought into contact with a sample, and thereafter, in the same manner as above, fluorescence emitted in a case where the sample is irradiated with the excitation light is detected, and thus the presence of the substance to be measured can be confirmed.

In the fluorescence detection method as described above, in order to improve detection sensitivity, a method utilizing the effect of electric field enhancement by plasmon resonance has been known. In this method, in order to generate plasmon resonance, a sensor chip including a metal film provided in a predetermined region on a transparent support is prepared. The excitation light is allowed to enter an interface between the support and the metal film from a side opposite to the metal film formation surface of the support at an angle equal to or greater than a total reflection angle. Surface plasmons are generated in the metal film by irradiation with the excitation light, fluorescence is enhanced by the electric field enhancement effect due to generation of the surface plasmons, and therefore a signal/noise ratio (S/N ratio) is improved. In the fluorescence detection method by surface plasmon excitation (Surface Plasmon Fluorescence, hereinafter, will be referred to as "SPF method"), a signal enhancement of about 10 times as compared with a fluorescence detection method by epi-excitation (hereinafter, will be referred to as "epifluorescence method") is obtained, and thus high sensitive measurement is possible.

A low molecular weight antigen (for example, thyroxine (T4), cortisol, and the like) in blood is rarely present alone and is present in a state of binding to a blood protein (for example, albumin and the like) in most cases. Therefore, in clinical diagnosis using an antigen-antibody reaction, it is necessary to dissociate the low molecular weight antigen from the blood protein, and sodium salicylate or the like is generally used as a dissociator.

A bile acid is a generic term for compounds which has a cholanic acid skeleton and is a steroid derivative found predominantly in the bile of mammals. Similarly to other low molecular weight antigens, in blood, the bile acid usually binds to a blood protein such as albumin, and to taurine, and such a bile acid is called a conjugated bile acid (a bile salt). There are generally ten types of the bile acid, but three types of a cholic acid, a deoxycholic acid, and a chenodeoxycholic acid are main types. A collection of a plurality compounds is called bile acids. The main role of the bile acids is to promote the formation of micelles in the digestive tract so as to promote the absorption of dietary fat.

A quantitative determination of serum bile acids in dogs and cats is recognized as an examination reflecting hepatocyte functions and enterohepatic circulation. For example, in dogs and cats which exhibit a high level of liver enzyme activity but are not accompanied with jaundice, the usefulness of the serum bile acids has been demonstrated in order to detect hepatobiliary diseases that require clinically definite diagnosis. In addition, a quantitative determination of fasting and postprandial bile acids has been recommended in order to increase a diagnostic rate in diagnosis of congenital portosystemic shunt. In a case where a concentration of bile acids shows a high value, acute hepatitis, chronic liver disease, cholestasis, intestinal bacterial overgrowth, portosystemic shunt (PSS), and the like are suspected, whereas intestinal malabsorption is suspected in a case where a concentration of bile acids shows a low value. As described above, in the diagnosis of dogs and cats, a concentration of bile acids is measured as an indicator reflecting hepatocyte functions and enterohepatic circulation, and a simple measurement method for bile acids is disclosed in Seibert et al., (2014), PeerJ, DOI 10.7717/peerj.539.

Meanwhile, in an assay for ligands in serum or other body fluids, it is desirable that the influence of interfering substances on observed signals is reduced, or the influence is completely eliminated. JP2001-513877A discloses that a salicylic acid or an 8-anilino-1-naphthalenesulfonic acid is used as a dissociator for dissociating ligand from a complex.

SUMMARY OF THE INVENTION

As described above, the quantitative determination of bile acids is carried out in the diagnosis of dogs and cats, and a measurement method using an enzyme method and a method using an enzyme reaction for coloring are also being used in a case of a large machine or a simple POCT (point of care testing) determination device. In the method using an enzyme reaction, an optimum temperature range of the reaction is very narrow, and thus it is necessary that a determination device is set to have an optimum temperature range for the enzyme reaction, leading to time requirement for adjustment to the optimum temperature such as after turning on the device and measuring under a low temperature environment, and there is a problem that a rapid measurement cannot be performed. In addition, because the bile acids, which are low molecular weight antigens, are present in blood in a state of binding to polymer components (blood proteins such as albumin), it is necessary that the bile acids are dissociated from the blood proteins by using a dissociator in order to quantitatively determining the bile acids. The dissociator has been required to sufficiently dissociate bile acid components from polymer components.

An object of the present invention is to provide a kit for quantitatively determining a bile acid, in which it is possible to improve measurement accuracy by sufficiently dissociating the bile acid from a polymer component, and to rapidly carry out a quantitative determination of the bile acid with high accuracy under various environments without being affected by environments for measuring the bile acid such as power activation and low temperature environment, and a method for quantitatively determining the bile acid.

In order to solve the problems, the inventors of the present invention have conducted extensive studies on a dissociator for efficiently dissociating a bile acid bound to albumin, have found that the problems can be solved by using a specific dissociator which is an ammonium salt in a dry state, and therefore have completed the present invention. That is, according to the present invention, the following invention is provided.

(1) A kit for quantitatively determining a bile acid in a biological sample, comprising: a compound represented by General Formula (I) in a dry state; a fluorescent particle that has a first binding substance capable of binding to the bile acid; and a substrate that has a detection region having a second binding substance capable of binding to any one of the bile acid and the first binding substance,

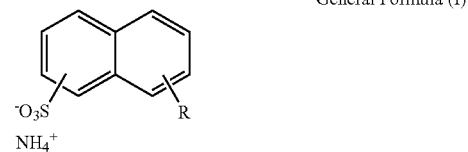

General Formula (I)

in the formula, R represents —NH—C$_6$H$_5$, —NH$_2$, or —NH—CH$_2$—CH$_2$—NH$_2$.

(2) The kit according to (1), in which in General Formula (I), a group represented by R is present at a 5-position, a 7-position, or an 8-position of a naphthalene ring, provided that substitution positions in the naphthalene ring are as follows.

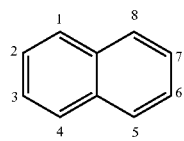

(3) The kit according to (1) or (2), in which in General Formula (I), R represents —NH—C$_6$H$_5$.

(4) The kit according to any one of (1) to (3), in which in General Formula (I), a group represented by —SO$_3^-$ is present at a 1-position or a 3-position of a naphthalene ring, provided that substitution positions in the naphthalene ring are as follows.

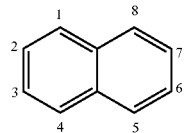

(5) The kit according to any one of (1) to (4), in which the substrate further has a reference region in which measurement for correcting data obtained in the detection region is performed.

(6) The kit according to any one of (1) to (5), in which the fluorescent particle that has the first binding substance capable of binding to the bile acid is a fluorescent colloidal particle having the first binding substance capable of binding to the bile acid.

(7) The kit according to (6), in which the fluorescent particle is a fluorescent latex particle.

(8) The kit according to any one of (1) to (7), in which the first binding substance capable of binding to the bile acid is at least three types of antibodies capable of binding to the bile acid.

(9) The kit according to (8), in which the at least three types of antibodies capable of binding to the bile acid include an anti-cholic acid antibody, an anti-deoxycholic acid antibody, and an anti-chenodeoxycholic acid antibody.

(10) A method for quantitatively determining a bile acid in a biological sample, the method comprising: a treatment step of treating a biological sample with a compound represented by General Formula (I) in a dry state; a reaction step of reacting the biological sample treated in the treatment step with a fluorescent particle having a first binding substance capable of binding to the bile acid; and a biological sample-related fluorescence information acquisition step of acquiring fluorescence information related to an amount of the biological sample,

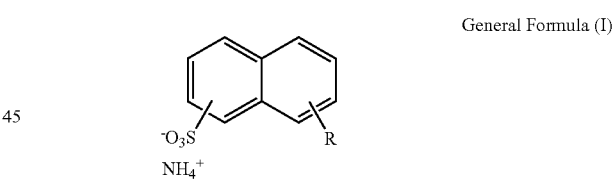

General Formula (I)

in the formula, R represents —NH—C$_6$H$_5$, —NH$_2$, or —NH—CH$_2$—CH$_2$—NH$_2$.

(11) The method according to (10), in which in General Formula (I), a group represented by R is present at a 5-position, a 7-position, or an 8-position of a naphthalene ring, provided that substitution positions in the naphthalene ring are as follows.

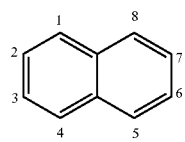

(12) The method according to (10) or (11), in which in General Formula (I), R represents —NH—C$_6$H$_5$.

(13) The method according to any one of (10) to (12), in which in General Formula (I), a group represented by —SO$_3^-$ is present at a 1-position or a 3-position of a naphthalene ring, provided that substitution positions in the naphthalene ring are as follows.

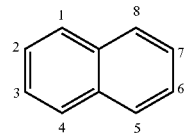

(14) The method according to any one of (10) to (13), further comprising: a fluorescent particle-related fluorescence information acquisition step of acquiring fluorescence information related to an amount of the fluorescent particle; and a standardization step of standardizing the fluorescence information acquired in the biological sample-related fluorescence information acquisition step by the fluorescence information acquired in the fluorescent particle-related fluorescence information acquisition step.

(15) The method according to any one of (10) to (14), in which the fluorescent particle that has the first binding substance capable of binding to the bile acid is a fluorescent colloidal particle having the first binding substance capable of binding to the bile acid.

(16) The method according to (15), in which the fluorescent particle is a fluorescent latex particle.

(17) The method according to any one of (10) to (16), in which the first binding substance capable of binding to the bile acid is at least three types of antibodies capable of binding to the bile acid.

(18) The method according to (17), in which the at least three types of antibodies capable of binding to the bile acid include an anti-cholic acid antibody, an anti-deoxycholic acid antibody, and an anti-chenodeoxycholic acid antibody.

According to the kit and the method of the present invention, it is possible to rapidly carry out the quantitative determination of the bile acid with high accuracy under various environments without being affected by environments for measuring the bile acid.

DESCRIPTION OF THE PREFERRED EMBODIMENTS

Figure 1:
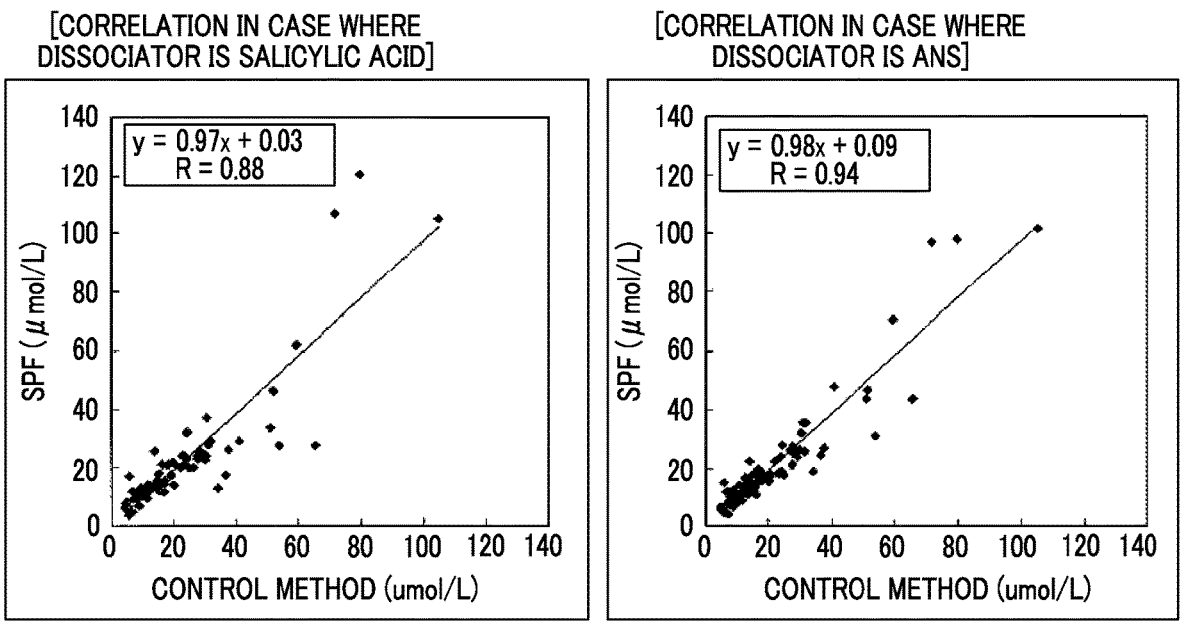
FIG. 1 shows a correlation in a case where a dissociator is a salicylic acid and a correlation in a case where the dissociator is Compound 1.

Hereinafter, the present invention will be described in detail.

[Kit for Quantitatively Determining Bile Acid in Biological Sample]

A kit for quantitatively determining a bile acid in a biological sample according to the present invention, including: a compound represented by General Formula (I) in a dry state; a fluorescent particle that has a first binding substance capable of binding to the bile acid; and a substrate that has a detection region having a second binding substance capable of binding to any one of the bile acid and the first binding substance.

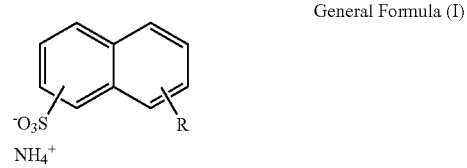

General Formula (I)

In the formula, R represents —NH—C$_6$H$_5$, —NH$_2$, or —NH—CH$_2$—CH$_2$—NH$_2$.

(Biological Sample)

The biological sample is not particularly limited as long as the biological sample is a sample which may contain the bile acids which are the substances to be measured, and examples thereof include a biological sample, particularly body fluids (for example, blood, blood serum, blood plasma, cerebrospinal fluid, tear fluid, sweat, urine, pus, nasal discharge, or expectoration) of animals (for example, humans, dogs, cats, and the like), excretas (for example, feces), organs, tissues, membrana mucosa, skin, and the like.

(Bile Acid)

There are ten types of bile acids, but in the case of dogs and cats, three types of a cholic acid, a deoxycholic acid, and a chenodeoxycholic acid account for almost 100% as bile acids. For example, a percentage of the three types of bile acids having different structures in blood of dogs is cholic acid:deoxycholic acid:chenodeoxycholic acid=74%:20%: 6%, in terms of average value (Journal of the Japanese Society of Veterinary Science, 52 (2), 1990). The structures of the cholic acid, the deoxycholic acid, and the chenodeoxycholic acid are as follows.

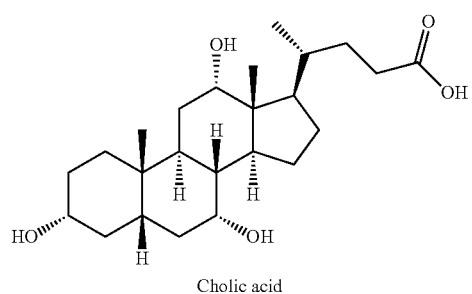

Cholic acid

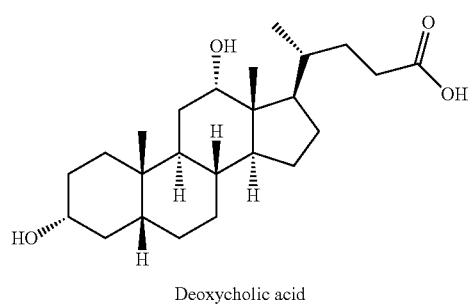

Deoxycholic acid

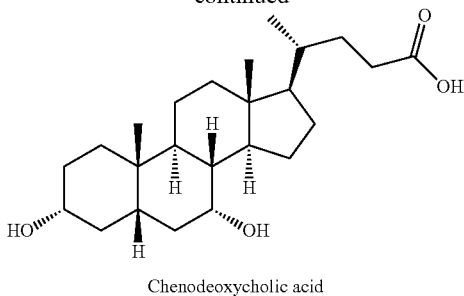

Chenodeoxycholic acid

A low molecular weight antigen (for example, thyroxine (T4), cortisol, and the like) in blood is rarely present alone and is present in a state of binding to a binding protein (for example, albumin, and the like) in most cases. Therefore, in clinical diagnostic drugs using antigen-antibody reaction, it is necessary to dissociate the low molecular weight antigen from the binding protein. The same applies to the bile acid and the bile acid is stably present in blood in a state of binding to albumin and the like. By using a compound represented by General Formula (I) which is an ammonium salt in a dry state as a dissociator for dissociation of this binding state, it is possible to improve measurement accuracy by sufficiently dissociating the bile acid from a polymer component; and to rapidly carry out the quantitative determination of the bile acid with high accuracy under various environments without being affected by environments for measuring the bile acid. It is presumed that the compound represented by General Formula (I) which is an ammonium salt in a dry state is capable of being sufficiently dissolved in blood serum and thus exhibits the above-described effect.

(Dissociator)

In the present invention, the compound represented by General Formula (I) is used as a dissociator.

In General Formula (I), a group represented by R represents an anilino group (—NH—$C_6H_5$), an amino group (—$NH_2$), or an ethylenediamino group (—NH—$CH_2$—$CH_2$—$NH_2$). A countercation of the sulfonic acid group is an ammonium ion ($NH_4^+$).

The represented by R is preferably an anilino group (—NH—$C_6H_5$) or an amino group (—$NH_2$), and is more preferably an anilino group (—NH—$C_6H_5$).

The represented by R may be present at any one of a 5-position, a 6-position, a 7-position, and an 8-position of a naphthalene ring, but is preferably present at the 5-position, the 7-position, or the 8-position, more preferably present at the 7-position or the 8-position, and particularly preferably present at the 8-position.

The represented by —$SO_3^-$ may be present at any one of a 1-position, a 2-position, a 3-position, and a 4-position of the naphthalene ring, but is preferably present at the 1-position or the 3-position, and more preferably present at the 1-position.

Provided that substitution positions in the naphthalene ring are as follows.

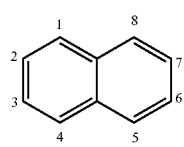

Specific examples of the compound represented by General Formula (I) include the following compounds.

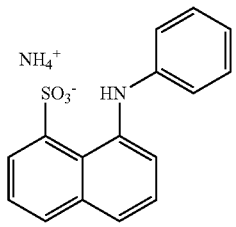

Compound 1

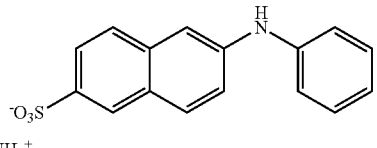

Compound 2

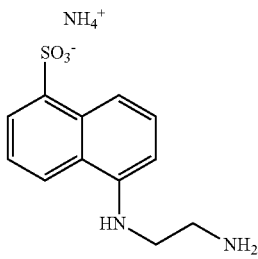

Compound 3

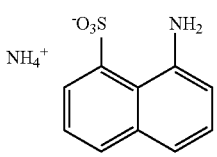

Compound 4

The dissociator in which the countercation is $NH_4^+$, which is represented by General Formula (I), has a high level of dissolution in blood serum of dogs, which is a great condition compared to a dissociator in which the countercation is $Mg^{2+}$ or $Na^+$, and therefore enables highly accurate measurement in the measurement of the bile acid using the electric field enhancement effect resulting from plasmon resonance. Compound 1 is commercially available from Tokyo Chemical Industry Co., Ltd. (catalog number: A5351, product name: ANS-NH4 (=Ammonium 8-Anilino-1-naphthalenesulfonate) [Hydrophobic fluorescent probe]).

In order to sufficiently dissociate the bile acid from the polymer component, an aspect in which the dissociator represented by General Formula (I) is mixed with a biological sample containing the bile acid in advance, is preferable. The dissociator is preferably stored in a dry state in a container so that the dissociator can be stably preserved, and an aspect in which the dissociator is dissolved in the container so as to exhibit a dissociate function when being mixed with a sample, is preferable. An amount used of the dissociator is 0.1 µmol or more, preferably 100 µmol or more, and more preferably 0.4 µmol to 50 µmol, per 1 mL of the biological sample.

The kit of the present invention contains the compound represented by General Formula (I) in a dry state. The term "dry state" means that a compound is not a solution but is the compound represented by General Formula (I) in a solid state, in which a moisture content is 30% by mass or less.

The moisture content is more preferably 20% by mass or less and even more preferably 15% by mass or less. The moisture content can be obtained by a weight measurement method.

(First Binding Substance)

The first binding substance used in the present invention is a substance capable of binding to the bile acid. The first binding substance is not particularly limited, but an antibody can be used. In a case where the first binding substance is an antibody, for example, an antiserum prepared from blood serum of an animal immunized with the bile acid, an immunoglobulin fraction purified from an antiserum, a monoclonal antibody obtained by cell fusion using spleen cells of an animal immunized with the bile acid, fragments thereof [for example, $F(ab')_2$, Fab, Fab', or Fv], and the like can be used. The preparation of these antibodies can be carried out by using a general method. Furthermore, an antibody modified as a case of a chimeric antibody or the like may be used, or a commercially available antibody also may be used as long as the antibody is an antibody prepared from blood serum of an animal or culture supernatant by a known method.

As described above, as the first binding substance, an anti-bile acid antibody that is capable of binding to the bile acid (preferably, specifically recognizes the bile acid) can be used. As the first binding substance capable of binding to the bile acid, at least three types of antibodies capable of binding to the bile acids may be used. That is, since the bile acids include the cholic acid, the deoxycholic acid, and the chenodeoxycholic acid, in the present invention, as the first binding substance, an anti-cholic acid antibody, an anti-deoxycholic acid antibody, and an anti-chenodeoxycholic acid antibody may be produced so as to be used as the three types of antibodies.

As a specific method for producing the anti-cholic acid antibody, the anti-deoxycholic acid antibody, and the anti-chenodeoxycholic acid antibody, a method for producing the anti-cholic acid antibody will be described below as an example.

It is possible to produce a cholic acid-BSA conjugate by mixing a cholic acid, bovine serum albumin (hereinafter will be abbreviated as BSA), and a condensing agent. The conjugate is used as a mouse immunizing antigen and a mouse is immunized subcutaneously several times on the back thereof. In this case, a complete adjuvant (Freund's Complete Adjuvant: FCA), and/or an incomplete adjuvant (Freund's Incomplete Adjuvant: FIA) can be appropriately selected and mixed with the immunizing antigen so as to be used. The complete adjuvant is a substance that stimulates immunity and is a mixture of paraffin and ARLACEL. The incomplete adjuvant is an adjuvant in which killed bacteria of dead mycobacteria or *Mycobacterium tuberculosis* are added to the complete adjuvant so as to further enhance antigenicity. After performing the immunization as appropriate for several times over several weeks, blood is collected from the mouse and antibody titers are measured. In a case where a sufficient increase in the antibody titers is observed, the antigen is administered intraperitoneally and the spleen is extracted several days later. By fusing the spleen cells extracted from the immunized mouse with mutant myeloma cell lines (myeloma), it is possible to produced hybrid cells having an antibody-producing ability. Among these hybrid cells, only cells producing an antibody against the target antigen are selected and subjected to limiting dilution so as to proliferate only the cell line thereof. Culturing (cloning) of the cells after dilution can be carried out. By intraperitoneally injecting the hybrid cell line obtained as above into the mouse so as to proliferate the ascites-type antibody-producing cells, it is possible to produce monoclonal antibodies in the ascites, and by recovering these antibodies, the target antibody can be obtained.

(Fluorescent Particle)

As the fluorescent particle used in the present invention, colored fluorescent particles which can be generally used for immunologic response can be used, and for example, fluorescent polymer particles such as fluorescent polystyrene beads, or fluorescent glass particles such as fluorescent glass beads can be used. Specific examples of a material of the fluorescent particles include synthetic polymer powders such as a polymer using a monomer such as styrene, methacrylic acid, glycidyl (meth)acrylate, butadiene, vinyl chloride, vinyl acetate acrylate, methyl methacrylate, ethyl methacrylate, phenyl methacrylate, or butyl methacrylate, or a copolymer using two or more kinds of monomers, and a latex in which these powders are uniformly suspended is preferred. In addition, other examples thereof include organic polymer powders and inorganic substance powders, microorganisms, blood cells and cell membrane pieces, liposomes, and the like.

The fluorescent particle having the first binding substance capable of binding to the bile acid is preferably a fluorescent colloidal particle having the first binding substance capable of binding to the bile acid.

In a case of using latex particles, specific examples of a material of the latex include polystyrene, styrene-acrylic acid copolymer, styrene-methacrylic acid copolymer, styrene-glycidyl (meth)acrylate copolymer, styrene-styrene sulfonic acid salt copolymer, methacrylic acid polymer, acrylic acid polymer, acrylonitrile-butadiene-styrene copolymer, vinyl chloride-acrylic acid ester copolymer, polyvinyl acetate acrylate, and the like. As the latex, a copolymer containing at least styrene as a monomer is preferable, and a copolymer of styrene and an acrylic acid or a methacrylic acid is particularly preferable. A method for producing the latex is not particularly limited, and the latex can be producing by any polymerization method. It is difficult to immobilize the antibody in a case where a surfactant is present in a case of antibody labeling, and therefore the production of the latex is preferably carried out by emulsion polymerization of a demulsifier, that is, emulsion polymerization without using an emulsifier such as a surfactant.

When the latex itself obtained by the polymerization is fluorescent, the latex can be used as the fluorescent latex particle as it is. In a case where the latex obtained by the polymerization is nonfluorescent, the fluorescent latex particle can be produced by adding a fluorescent substance (such as a fluorescent dye) to the latex. That is, the fluorescent latex particle can be produced by adding the fluorescent dye to a solution of latex particles containing water and a water-soluble organic solvent and stirring the same.

Liposomes, microcapsules, or the like which contain the fluorescent dye can also be used as the fluorescent particles. Fluorescence coloring is not particularly limited as long as the fluorescence coloring is released in a case of absorbing and exciting ultraviolet light or the like and returning to a ground state. For example, the fluorescence coloring such as yellow green (excitation wavelength 505 nm/emission wavelength 515 nm, hereinafter the same applies), blue (350 to 356 nm/415 to 440 nm), red (535 to 580 nm/575 to 605 nm), orange (540 nm/560 nm), red orange (565 nm/580 nm), crimson (625 nm/645 nm), dark red (660 nm/680 nm), and the like, may be used. These fluorescent particles emitting fluorescence are available from, for example, Thermo Fisher and are commercially available on the market under the trade name of FluoSpheres (registered trademark) of the same company.

An average particle diameter of the fluorescent particles varies depending on the material of the particles, a concentration range for the quantitative determination of the bile acid, a measuring instrument, and the like, but is preferably within the range of 0.001 to 10 µm (more preferably 0.001 to 1 µm).

(Method for Measuring Average Particle Diameter)

The average particle diameter of the fluorescent particles can be measured with a commercially available particle size distribution meter or the like. As a method for measuring the particle size distribution, optical microscopy, confocal laser microscopy, electron microscopy, atomic force microscopy, static light scattering method, laser diffraction method, dynamic light scattering method, centrifugal sedimentation method, electric pulse measurement method, chromatography method, ultrasonic attenuation method, and the like are known, and devices corresponding to the respective principles are commercially available.

From the viewpoint of the particle size range and the ease of measurement, it is preferable to use the dynamic light scattering method in the present invention. Commercially available determination devices using dynamic light scattering include NANOTRAC UPA (Nikkiso Co., Ltd.), dynamic light scattering type particle size distribution determination device LB-550 (Horiba Seisakusho), concentrated system particle size analyzer FPAR-1000 (Otsuka Electronics Co., Ltd.), ZETASIZER Nano series (Malvern Instruments Inc.), and the like, and in the present invention, a median diameter (d=50) measured at a measuring temperature of 25° C. is obtained.

(First Binding Substance on Surface of Fluorescent Particle)

In a case where three or more types of the binding substances (for examples, the anti-cholic acid antibody, the anti-deoxycholic acid antibody, and the anti-chenodeoxycholic acid antibody) are used as the first binding substance, it is possible that the binding substances are adsorbed to the surface of one fluorescent latex particle so as to be used. In this case, each fluorescent particle of the fluorescent particles to be used has the above three types of the binding substances. Alternatively, a fluorescent latex particle to which one type (for example, the anti-cholic acid antibody) among the three or more types of the binding substances is adsorbed, a fluorescent latex particle to which another one (for example, the anti-deoxycholic acid antibody) among the three or more types of the binding substances is adsorbed, and a fluorescent latex particle to which the other one type (for example, the anti-chenodeoxycholic acid antibody) among the three or more types of the binding substances is adsorbed, may be produced respectively so as to use a mixture of the above three types of the fluorescent latex particle.

Preferably, the three or more types of the binding substances used as the first binding substance can be used by being adsorbed to the surface of the one fluorescent particle (each fluorescent particle). The bile acid is an aggregate of a plurality of different substances, but it is preferable to use the fluorescent particles having all the binding substances to which each different substance binds. As one embodiment of the present invention, the fluorescent particles having all of the anti-cholic acid antibody, the anti-deoxycholic acid antibody, and the anti-chenodeoxycholic acid antibody can be used. With the above configuration, it becomes possible that all fluorescent particles interact with all of the bile acids (that is, the cholic acid, the deoxycholic acid, and the chenodeoxycholic acid) composed of different substances present in a biological sample. Therefore, it is preferable that the at least three types of the binding substances bind to each fluorescent particle. In a case of using antibody-conjugated fluorescent particles, the quantitative determination of the bile acid can be carried out by using one type of the fluorescent particles for one biological sample, excluding inter-particle distribution of the number of antibody conjugates.

(Modification of Fluorescent Particles with First Binding Substance)

A method for immobilizing the first binding substance on the fluorescent particle is described in protocols and the like attached to, for example, JP2000-206115A and FluoSpheres (registered trademark) polystyrene microsphere F8813 manufactured by Thermo Fisher, and any known methods for preparing a reagent for immunoagglutination reaction can be used. In addition, as a principle of immobilizing an antibody as a binding substance to particles, any principle of physical adsorption and chemical bond by covalent bond can be adopted. As a blocking agent which covers the surface of the particle not coated with the antibody after the antibody is immobilized on the particles, it is possible to use a commercially available blocking agent for immunologic response, which contains the above-described substances or substances having the same properties as the above-described substance, which are known substances such as BSA, skim milk, casein, soy-derived components, fish-derived components, polyethylene glycol, and the like. These blocking agents can also be subjected to a pretreatment such as partial denaturation by heat, acid, alkali, or the like, as necessary.

Specific methods for immobilizing the antibody to particles are exemplified below. An antibody solution adjusted to have a concentration of 0.01 to 20 mg/mL is added to and mixed with a solution in which the particles are dispersed so that a concentration of solid contents of the particles becomes 0.1% to 10% by mass. The mixture is continuously stirred for 5 minutes to 48 hours under a temperature of 4° C. to 50° C. Subsequently, the particles and the solution are dissociated from each other by centrifugation or other methods so as to sufficiently remove the antibody which has not bind to the particles in the solution. Thereafter, the operation of washing the particles with a buffer solution is repeated 0 to 10 times. After carrying out the operation of mixing the particles with the antibody and allowing the antibody to bind to the particles, it is desirable to protect a portion of the particle surface to which the antibody has not bind by using a blocking agent such as components not involved in antigen-antibody reaction, preferably proteins, more preferably BSA, BLOCK ACE (registered trademark), skim milk, and casein.

In a case of immobilizing antigens, antibodies, and the like to particles, stabilizers can be added as necessary. The stabilizer is not particularly limited as long as the stabilizer stabilizes antigens and antibodies, such as synthetic polymers such as sucrose and polysaccharides, or natural polymers. Commercially available stabilizers such as Immunoassay Stabilizer (Advanced Biotechnologies Inc. (ABI)), and the like can also be used.

(Substrate)

In the present invention, in order to achieve highly sensitive measurement, it is preferable to adopt a measurement method that performs surface plasmon fluorescence (SPF) detection to be described below. As a substrate in this case, it is preferable to use a substrate having a metal film on a surface thereof. A metal constituting the metal film is not particularly limited as long as it is a metal by which surface plasmon resonance can occur. Preferable examples thereof include free electron metals such as gold, silver, copper, aluminum, or platinum, and gold is particularly preferable. In a case where gold is used, a detection region to be described below becomes a gold film surface. These metals can be used alone or in combination. Furthermore, in consideration of adhesion to the substrate, an intermediacy layer made of chromium or the like may be provided between the substrate and a layer formed of the metal. Any thickness of the metal film may be used, but is preferably, for example, 1 nm to 500 nm, and particularly preferably 10 nm to 200 nm. In a case where the thickness exceeds 500 nm, the surface plasmon phenomenon of a medium cannot be sufficiently detected. In addition, in a case of providing the intermediacy layer made of chromium or the like, the thickness of the intermediacy layer is preferably 0.1 nm to 10 nm.

The formation of the metal film may be carried out by a general method and can be carried out by, for example, a sputtering method, a vapor deposition method, an ion plating method, an electroplating method, an electroless plating method, or the like, but in order to improve the adhesiveness of the metal film by providing a mix layer of the substrate material and the metal film, it is preferable to prepare the metal film by the sputtering method. In this case, a thickness of the mix layer of the substrate material and the metal film is not particularly limited as long as sufficient adhesiveness can be secured, but is preferably 10 nm or less.

The metal film is preferably disposed on the substrate. The term "disposed on the substrate" means not only that the metal film is disposed in direct contact with the substrate, but also that the metal film is disposed via other layers without in direct contact with the substrate. As a material of the substrate which can be used in the present invention, for example, optical glass such as BK7 (borosilicate glass) which is one of general optical glasses, or synthetic resin, specifically, polymethyl methacrylate, polyethylene terephthalate, polycarbonate, cycloolefin polymer, or the like which is transparent to laser light can be used. It is desirable that such a substrate has a material which does not exhibit anisotropy with respect to polarized light and has excellent workability.

As a preferred aspect of the substrate for detecting SPF, there is a substrate obtained by vapor-depositing a gold film on polymethyl methacrylate (PMMA), and the like.

The substrate has a detection region having a second binding substance capable of binding to any one of the bile acid and the first binding substance.

(Second Binding Substance)

The second binding substance is a substance capable of binding to the bile acid or is a substance capable of binding to the first binding substance. In a case where the quantitative determination is carried out by a sandwich assay method, the substance capable of binding to the bile acid can be used as the second binding substance. In a case where the quantitative determination is carried out by a competitive method, the substance capable of binding to the first binding substance can be used as the second binding substance. In the present invention, it is preferable to carry out the quantitative determination by a competitive method, and it is preferable to use the substance capable of binding to the first binding substance as the second binding substance.

The second binding substance is not particularly limited, but preferable examples thereof include an antigen, an antibody, or a complex thereof. The second binding substance is preferably an antigen, and the bile acid (which is the substance capable of binding to the first binding substances) is particularly preferably used as the second binding substance.

In a case where the bile acid is used as the second binding substance, the second binding substance is preferably a substance having at least three different structures constituting the bile acid (such as cholic acid, deoxycholic acid, and chenodeoxycholic acid), or a conjugate of the above three types of substances having different structures and a carrier. The term "carrier" means a substance to which a plurality of molecules of at least three types of substances to be measured can bind. A preferable second binding substance is an aspect including at least three types of conjugates in which a plurality molecules of the same type of substances to be measured bind to one molecule carrier. Preferable examples of the carrier include proteins and the like, and specific examples include bovine serum albumin and the like.

In the present invention, it is particularly preferable the second binding substance includes a cholic acid and/or a cholic acid-albumin conjugate, a deoxycholic acid and/or a deoxycholic acid-albumin conjugate, and a chenodeoxycholic acid and/or a chenodeoxycholic acid-albumin conjugate.

(Method for Immobilizing Second Binding Substance on Substrate)

A method for immobilizing the second binding substance on the substrate is described in, for example, Tech Notes Vol. 2-12 and the like provided by Nunc, and any known methods for preparing a general ELISA (Enzyme-Linked ImmunoSorbent Assay) reagent can be used. In addition, surface modification may be performed by disposing a self-assembled monolayer (self-assembled monolayer: SAM) or the like on the substrate, and any method of a method using physical adsorption and a method using chemical bonds by covalent bonds can be adopted as a method for immobilizing the second binding substance on the substrate. As a blocking agent which covers the surface of the substrate not coated with the second binding substance after the second binding substance is immobilized on the substrate, it is possible to use a commercially available blocking agent for immunologic response, which contains the above-described substances or substances having the same properties as the above-described substance, which are known substances such as BSA, skim milk, casein, soy-derived components, fish-derived components, polyethylene glycol, and the like. These blocking agents can also be subjected to a pretreatment such as partial denaturation by heat, acid, alkali, or the like, as necessary.

(Detection Region <Test Area>)

In the present invention, a test area for detecting the presence or absence of the bile acid in the biological sample can be provided on the substrate. In this test area, it is possible to quantitatively determine the bile acid by, for example, capturing the bile acid and detecting and quantitatively determining an amount of label bound to the bile acid. Alternatively, it is possible to quantitatively determine the bile acid by a method of preventing only a label bound to the bile acid from binding, capturing only a label not bound to the bile acid, and calculating an amount of label bound to the bile acid. This detection method is called a competitive method, and the substrate relating to the competitive method will be explained.

In the test area of the substrate, it is preferable to provide sites reacting with all the binding substances (for example, antibodies) present on the fluorescent particles. As a preferable aspect of the present invention, an aspect in which the bile acid present in the sample is provided on the test area of the substrate is preferable. In this case, it is possible to produce the test area by reacting the bile acid with BSA in the presence of a condensing agent to produce a bile acid-BSA conjugate and adsorbing this conjugate on the test area. In this case, it is preferable that the three types of the bile acids (cholic acid, deoxycholic acid, and chenodeoxycholic acid)-BSA conjugate are randomly mixed so as to be disposed on the test area. It is possible that the bile acids-BSA conjugate is dissolved in a buffer solution, spotted onto the substrate, and left alone for a certain period of time, and then the supernatant is aspirated and bound to the test area on the substrate by a method such as drying.

(Reference Region <Control Area>)

In the present invention, in order to minimize the influence of the measurement environment, particularly the measurement temperature, a control area is provided on the substrate and information of the test area is standardized by information of the control area, and therefore it is possible to suppress environment dependency to a significantly low level. The reference region (control area) is a region for performing measurement for correcting data obtained in the detection region. It is preferable that the control area is designed such that the control area can be combined with all the labels irrespective of an amount of the substances to be measured which are to be detected in the biological sample to be used. It is preferable that an antibody which interacts with all the antibodies present on the fluorescent particles which are labels, is provided. With such a design, by standardizing the information of the test area with the information of the control area, even in a case where the flow of the biological sample or the reaction rate is influenced by, for example, a low temperature environment, it is possible to cancel the influence by standardization and to obtain a result which is not influenced by the measurement environment with high accuracy at all cases.

As a preferable antibody to be present in the control area, an anti-mouse antibody is preferable as long as an anti-mouse antibody has a function of recognizing the three or more types of the binding substances (for example, antibodies) present on the fluorescent particles and is derived from a mouse, and in a case where the antibody on the fluorescent particle is derived from a goat, an anti-goat antibody is preferable. It is possible that these antibodies on the control area are dissolved in a buffer solution, spotted onto the substrate, and left alone for a certain period of time, and then the supernatant is aspirated and bound to the substrate by a method such as drying.

(Nonspecific Adsorption Preventing Substance)

In the reagent kit of the present invention, it is preferable to further modify the fluorescent particles with a substance which does not specifically bind to the bile acid or with the binding substance. For example, in the competitive method, not only a negative biological sample that does not contain the bile acid, but also a biological sample that also reacts to a positive biological sample containing the bile acid so as to become negative, exists, and a solution to a high value dissociation problem is recognized as an object. Although the cause of such false negative is not clarified, it is considered that the presence of the fluorescent particle, which is not to be bound, due to nonspecific interaction between the surface of the fluorescent particle not covered with the antibody and the detection region (test area), is one of the reasons. In addition, even in a case where the same substance as the substance present on the test area is present on the surface of the fluorescent particle, in a case where a liberated antibody or the like is present in the biological sample, there is a case in which this antibody binds to any one of the substance present on the test area and the substance on the surface of the fluorescent particle, and thus a case in which a positive biological sample containing the bile acid is measured, is also detected as negative. In general, blocking with BSA is used for suppressing nonspecific adsorption to a solid surface (for example, the surface of the fluorescent particle, a gold film surface of the substrate), but in a case where an anti-BSA antibody reacting with BSA is present in a specific biological sample, BSA on the fluorescent particle reacts with BSA on the substrate so as to be crosslinked, and high value dissociation occurs in some cases. Therefore, as a preferable binding substance, it is preferable to use a substance which does not specifically bind to the bile acid and does not bind to a causative substance exhibiting false negative as described above. Antibodies that do not bind to the bile acids, proteins not to be used in the test area (Protein A, Protein G), or the like can be used as the binding substance, among which the antibodies that do not bind to the bile acids is preferable. Specifically, an antiserum prepared from blood serum of an animal immunized with an antigen different from bile acid, an immunoglobulin fraction purified from an antiserum, a monoclonal antibody obtained by cell fusion using spleen cells of an animal immunized with the bile acid, fragments thereof [for example, F(ab)$_2$, Fab, Fab, or Fv], and the like can be used. The preparation of these antibodies can be carried out by using a general method. Furthermore, an antibody modified as a case of a chimeric antibody or the like may be used, or a commercially available antibody also may be used as long as the antibody is an antibody prepared from blood serum of an animal or culture supernatant by a known method. In the present invention, an aspect in which an anti-CRP (C-reactive protein) antibody is used as the binding substance is particularly preferable.

(Antibody)

In the present invention, the antibody can be used regardless of animal species or subclass thereof. For example, the antibody that can be used in the present invention is an antibody derived from an organism in which an immunologic response can occur, such as mouse, rat, hamster, goat, rabbit, sheep, cow, and chicken. Specific examples thereof include mouse IgG, mouse IgM, rat IgG, rat IgM, hamster IgG, hamster IgM, rabbit IgG, rabbit IgM, goat IgG, goat IgM, sheep IgG, sheep IgM, bovine IgG, bovine IgM, avian IgY, and the like, and both polyclonal and monoclonal antibodies can be used. Fragmented antibodies are molecules derived from intact antibodies having at least one antigen binding site, and specific examples thereof include Fab, F(ab')$_2$ and the like. These fragmented antibodies are molecules obtained by enzymatic or chemical treatment or using genetic engineering techniques.

(Other Components of Kit)

The kit of the present invention is used for the method for measuring the bile acid, and is a kit for diagnosis of the bile acid measurement. In a case of carrying out the measurement of the bile acid in the present invention, the sensor chip including a substrate on which the second binding substance such as a bile acid-albumin conjugate is immobilized; a first container having the compound represented by General Formula (I) in a dry state; and a second container that is a member for retaining the fluorescent particle, is provided, but various devices or instruments used for measuring the bile acids such as surface plasmon excitation devices and fluorescence measurement devices may be included. Furthermore, as a component of the kit, a sample containing a bile acid of a known amount, an instruction manual, and the like may be included.

[Method for Quantitatively Determining Bile Acid in Biological Sample]

A method for quantitatively determining a bile acid in a biological sample of the present invention, includes a treatment step of treating a biological sample with a compound represented by General Formula (I) in a dry state; a reaction step of reacting the biological sample treated in the treatment step with a fluorescent particle having a first binding substance capable of binding to the bile acid; and a biological sample-related fluorescence information acquisition step of acquiring fluorescence information related to an amount of the biological sample.

The treatment step of treating the biological sample with the compound represented by General Formula (I) in a dry state, can be carried out by mixing the biological sample (usually in a liquid state) with the compound represented by General Formula (I) in a dry state, and dissolving the compound represented by General Formula (I) in the biological sample (liquid). The compound represented by General Formula (I) in a dry state is included in the kit of the present invention, and an aspect in which the compound is contained in the container which is a part of the kit, for example, in a cup, is preferable, and the above-described treatment step can be carried out in the inside of the cup. The environmental conditions for carrying out the above treatment step are not particularly limited, but the step can be generally carried out at 0° C. to 40° C., preferably at 10° C. to 30° C.

The fluorescent particles having the first binding substance are included in the kit of the present invention, and an aspect in which the fluorescent particles are contained in the container which is a part of the kit, for example, in a cup, is preferable, and an aspect in which this container is different from the container containing the compound represented by General Formula (I) in a dry state, is preferable. The reaction step of reacting the biological sample treated in the treatment step with the fluorescent particle having the first binding substance capable of binding to the bile acid, can be carried out by injecting a solution obtained by dissolving the compound represented by General Formula (I) in the biological sample (liquid) into the container containing the fluorescent particles, so as to be mixed with the fluorescent particle having the first binding substance capable of binding to bile acid, and stirring the same.

The bile acid is quantitatively determined by a biological sample-related fluorescence information acquisition step of acquiring fluorescence information related to an amount of the biological sample.

The quantitative determination in the present invention is interpreted as the broadest concept as long the quantitative determination is measurement of an amount of the bile acid. Specific aspects of the measurement method include the competitive method and the sandwich method, but the competitive method is preferable.

An example of the competitive method is described below.

In the competitive method, first, in a bile acid immunoassay substrate on which a bile acid-albumin conjugate having a bile acid/albumin ratio of 7 to 14 is immobilized, the biological sample containing the bile acid is contacted with an anti-bile acid antibody-labeled fluorescent particle. In a case where the bile acid is not present in the biological sample, an antigen-antibody reaction occurs on the substrate by the anti-bile acid antibody-labeled fluorescent particle and the bile acid on the substrate (that is, the bile acid in the bile acid-albumin conjugate). On the other hand, in a case where the bile acid is present in the biological sample, an antigen-antibody reaction occurs between the bile acid in the biological sample and the anti-bile acid antibody-labeled fluorescent particle, and an antigen-antibody reaction is inhibited between the bile acid (for example, the bile acid in the bile acid-albumin conjugate) on the substrate and the anti-bile acid antibody-labeled fluorescent particle. After completion of the above reaction, anti-bile acid antibody-labeled fluorescent particles not bound to albumin on the substrate are removed. Subsequently, by detecting a degree of formation of immune complexes on the substrate (that is, a complex of the anti-bile acid antibody-labeled fluorescent particle and the bile acid in the bile acids-albumin conjugate on the substrate) as fluorescence intensity, it is possible to measure a concentration of the bile acid in the biological sample, and the like.

As a measurement form of fluorescence in the competitive method, it is possible to adopt any one of plate reader measurement and flow measurement, and for example, the measurement can be carried out by the following method. A plurality of samples with known amounts of the bile acid differing in bile acid concentration is prepared in advance, and this sample is mixed with the anti-bile acid antibody-labeled fluorescent particles in advance. This mixed solution is brought into contact with a region on which the bile acid-albumin conjugate is immobilized. A fluorescent signal from the region on which the bile acid-albumin conjugate is immobilized is measured as a plurality of fluorescent signals while the mixed solution is in contact with the conjugate at specific time intervals. Based on the plurality of fluorescent signals, a time change (inclination) of the amount of fluorescence is obtained at each bile acid concentration. By plotting this time change as a Y-axis and the bile acid concentration as an X-axis, a relational expression of the bile acid concentration with respect to the time change in the fluorescence amount is acquired by using an appropriate fitting method such as a least squares method or the like. Based on the relational expression thus obtained, the amount of bile acid contained in the biological sample can be quantitatively determined by using the result of the time change of the amount of fluorescence using the biological sample to be examined.

The quantitative determination of the amount of bile acid is preferably carried out in a short period of time. Specifically, the quantitative determination is preferably carried out within 10 minutes, more preferably within 8 minutes, and even more preferably within 6 minutes. By using the relational expression between the time change in the amount of fluorescence and the bile acid concentration acquired in advance using an appropriate fitting method such as the least squares method or the like, the sample and the anti-bile acid antibody-labeled fluorescent particle are brought into contact with the detection region to which the bile acid-albumin conjugate is immobilized, and then a time for converting the amount of bile acid contained in the biological sample is obtained based on the result of the time change of the fluorescence amount using the biological sample to be examined, and a time for the quantitative determination preferably includes this time for conversion.

The sandwich method is not particularly limited, and for example, the bile acid can be measured by the following procedure. A biological sample that may contain the bile acid and the fluorescent particle having the first binding substance capable of binding to the bile acid are brought into contact with each other on the substrate. In a case where the bile acid is present in the biological sample, a binding reaction (such as an antigen-antibody reaction) occurs between the bile acid, the fluorescent particle, and the substrate. As a result, in a case where the bile acid is present in the biological sample, an immune complex composed of the second binding substance bound to the substrate, the bile acid, and the fluorescent particles having the first binding substance is formed. In the sandwich method, after completion of the reaction between the second binding substance, the bile acid, and the fluorescent particle having the first binding substance, the fluorescence having the first binding substance, in which the immune complex has not been formed, is removed and washed. Subsequently, the concentration of bile acid or the like can be measured by detecting a degree of immune complex formation as fluorescence intensity. The fluorescence intensity and the concentration of bile acid have a positive correlation.

(Flow Passage)

In a preferable aspect of the present invention, a mixed solution obtained by mixing the biological sample that may contain the bile acid and the fluorescent particles having the first binding substance can be applied on the substrate and developed in a flow passage. The flow passage is not particularly limited as long as it is a passage that allows the biological sample and the fluorescent particle having the first binding substance to flow down to the detection region. Preferable aspects of the flow passage include a spotting port for spotting the biological sample solution containing the fluorescent particles having the first binding substance, the metal film as the detection region, and a flow passage beyond the metal film. The biological sample has a structure capable of passing over the metal film. Preferably, a suction port can be provided on the side opposite to the spotting port with respect to the metal film.

(Measurement of Surface Plasmon Fluorescence)

A method for detecting fluorescence in the present invention is not particularly limited, and examples thereof include a device capable of detecting fluorescence intensity. Specifically, it is preferable to detect fluorescence intensity using a microplate reader, or biosensor for performing fluorescence detection (SPF) by surface plasmon excitation. The form of measurement of fluorescence may be plate reader measurement or flow measurement. The fluorescence detection method (SPF method) by surface plasmon excitation can perform the measurement with higher sensitivity than the fluorescence detection method (epifluorescence method) by epi-excitation.

As a surface plasmon fluorescence (SPF) biosensor, for example, it is possible to use a sensor, which is described in JP2008-249361A, the sensor including an optical waveguide formed from a material that transmits excitation light of a predetermined wavelength, a metal film formed on one surface of this optical waveguide, a light source for generating a light beam, an optical system that allows the light beam to pass through the optical waveguide and causes the light beam to enter the interface between the optical waveguide and the metal film at an incident angle that generates surface plasmons, and a fluorescence detection means for detecting the fluorescence generated by being excited by the above-described evanescent wave enhanced by the surface plasmon.

The fluorescence detection (SPF) system by surface plasmon excitation using the fluorescent particles of the present invention is a preferably an assay method for detecting fluorescence from the fluorescent substance dependent on the amount of bile acid immobilized on the metal film on the substrate, which is the method different from a so-called latex agglutination method in which a change in optical transparency is detected as, for example, turbidity due to progress of reaction in a solution. In the latex agglutination method, an antibody-sensitized latex in the latex reagent and the antigen in the biological sample bind and aggregate by an antibody reaction. The latex agglutination method is a method in which the agglomerate increases with time, and an antigen concentration is quantitatively determined from a change in absorbance per unit time obtained by irradiating the aggregate with near infrared light. In the present invention, it is possible to provide a significantly simple method for detecting the bile acid as compared with the latex agglutination method.

(Standardization)

The method of the present invention further includes a biological sample-related fluorescence information acquisition step of acquiring fluorescence information related to the bile acid in the biological sample; a fluorescent particle-related fluorescence information acquisition step of acquiring fluorescence information related to an amount of the fluorescent particle; and a standardization step of standardizing the fluorescence information acquired in the biological sample-related fluorescence information acquisition step by the fluorescence information acquired in the fluorescent particle-related fluorescence information acquisition step.

In steps in which a mixed solution containing the biological sample treated with the compound represented by General Formula (I) and the fluorescent particle having the first binding substance capable of binding to the bile acid is brought in contact with the substrate having the detection region (test area) and the reference region (control area) so as to generate surface plasmon on the detection region and the reference region, thereby measuring the intensity of the emitted fluorescence, a step of measuring the fluorescence intensity due to the surface plasmon generated on the detection region is the biological sample-related fluorescence information acquisition step, and a step of measuring the fluorescence intensity due to the surface plasmon generated on the reference region is the fluorescent particle-related fluorescence information acquisition step. A step in which an increase rate of the fluorescence intensity obtained in the two steps in unit time is obtained as a change rate of a fluorescence signal value, and a change rate of a signal value of the detection region is divided by a change rate of a signal value of the reference region, is the standardization step.

The present invention will be more specifically described with reference to the following examples, but the present invention is not limited by the examples.

EXAMPLES

Example 1

(1) Preparation of Bile Acid-Bovine Serum Albumin Conjugate (1-1) Preparation of Cholic Acid-Bovine Serum Albumin Conjugate To 1.2 mL of super dehydrated dimethylformamide (hereinafter, will be referred to as DMF, manufactured by Wako Pure Chemical Industries, Ltd.), 50 mg of cholic acid (manufactured by Wako Pure Chemical Industries, Ltd.) and 67 mg of N-hydroxysuccinimide (hereinafter, will be referred to as NHS, manufactured by Wako Pure Chemical Industries, Ltd.), and 110 mg of 1-ethyl-3-(3-dimethylaminopropyl)carbodiimide (hereinafter, will be referred to as EDC, manufactured by Wako Pure Chemical Industries, Ltd.) were added so as to be mixed, and therefore a cholic acid was actively esterified. This actively esterified cholic acid was dropwise added to and reacted with an aqueous solution of a 65 mL of a phosphate buffer solution (hereinafter, will be referred to as PBS, manufactured by Wako Pure Chemical Industries, Ltd.) in which 322 mg of bovine serum albumin (hereinafter, will be referred to as BSA, manufactured by Wako Pure Chemical Industries, Ltd.) as one type of albumin was dissolved. After completion of the reaction, the reaction solution was purified by dialysis using 1 L of a solution in which a ratio of acetonitrile (hereinafter, will be referred to ACN, manufactured by Wako Pure Chemical Industries, Ltd.)/water was 1/3. Finally, freeze-drying was carried out, and therefore a white solid was obtained.

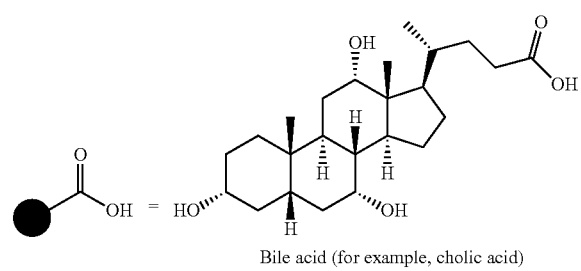

Bile acid (for example, cholic acid)

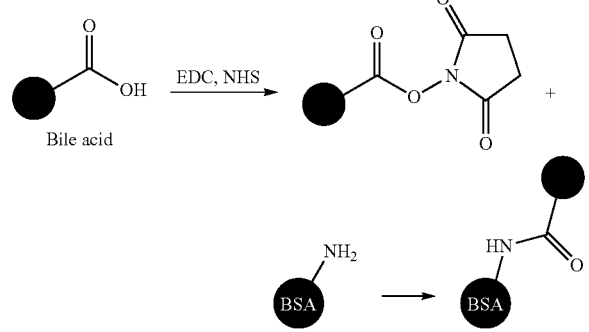

(1-2) Preparation of Deoxycholic Acid-BSA Conjugate 50 mg of deoxycholic acid (manufactured by Wako Pure Chemical Industries, Ltd.), 67 mg of NHS, and 110 mg of EDC were added to 1.2 mL of super dehydrated DMF so as to be mixed, and therefore the deoxycholic acid was actively esterified. This actively esterified deoxycholic acid was added dropwise to and reacted with an aqueous solution of 65 mL of PBS in which 322 mg of BSA was dissolved. After completion of the reaction, the reaction solution was purified by dialysis using 1 L of a solution in which a ratio of ACN/water was 1/3. Finally, freeze-drying was carried out, and therefore a white solid was obtained.

(1-3) Preparation of Chenodeoxycholic Acid-BSA Conjugate 50 mg of chenodeoxycholic acid (manufactured by Wako Pure Chemical Industries, Ltd.), 67 mg of NHS, and 110 mg of EDC were added to 1.2 mL of super dehydrated DMF so as to be mixed, and therefore the chenodeoxycholic acid was actively esterified. This actively esterified chenodeoxycholic acid was added dropwise to and reacted with an aqueous solution of 65 mL of PBS in which 322 mg of BSA was dissolved. After completion of the reaction, the reaction solution was purified by dialysis using 1 L of a solution in which a ratio of ACN/water was 1/3. Finally, freeze-drying was carried out, and therefore a white solid was obtained.

(2) Measurement of Mole Ratio of Bile Acid/BSA Label (Bile Acid/Albumin Ratio of Conjugate) by MALDI-TOF-MS (Matrix-Assisted Laser Desorption Ionization-Time of Flight Mass Spectrometry)

(Measurement Procedure)

The conjugates prepared in (1-1) to (1-3) were dissolved in a solution in which a ratio of 0.1% by mass of trifluoroacetic acid (TFA):ACN is 2:1, and a concentration was adjusted to 1 mg/mL. 1 µL of this solution and 4 µL of matrix (sinapinic acid: SA (manufactured by Wako Pure Chemical Industries, Ltd.)) were mixed and 4 points were spotted as 1 µL on a gold plate. After drying naturally, a gold plate was inserted into a MALDI-TOF-MS apparatus (Applied Bio Systems, Inc. Voyager), 900 shots were accumulated per spot, and therefore data as mass information was obtained (N=4). Using this data, a molecular weight center value at 50% intensity of a maximum value of the peak intensity of the peak corresponding to the bile acid-BSA conjugate was adopted as the peak of the BSA conjugate, and a point where the peak value was lowered vertically was set as a molecular weight of the bile acid-BSA conjugate so as to obtain an average value of N=4, and therefore the number of bile acids binding to BSA was calculated by (molecular weight of bile acid-BSA conjugate−molecular weight of native BSA)/molecular weight of bile acid (for example, in a case of cholic acid, 408−18=390). The bile acid/BSA ratio of the obtained conjugate is shown in Table 1.

TABLE 1

| Conjugate | Bile acid-BSA conjugate | Bile acid/BSA mole ratio |
|---|---|---|
| Conjugate-1 | Cholic acid-BSA | 13 |
| Conjugate-2 | Deoxycholic acid-BSA | 13 |
| Conjugate-3 | Chenodeoxycholic acid-BSA | 13 |

(3) Production of Hybridomas for Producing Cholic Acid Antibody, Deoxycholic Acid Antibody, or Chenodeoxycholic Acid Antibody, and Antibody Production (3-1) Immunogen 2 mg each of the cholic acid-BSA conjugate, the deoxycholic acid-BSA conjugate, and the chenodeoxycholic acid-BSA conjugate produced above was used as an immunogen for mouse immunization.

(3-2) Preparation of Hybridoma

As the immunogen for mouse immunization, the cholic acid-BSA conjugate was used.

The cholic acid-BSA conjugate was subcutaneously administered to a mouse so as to carry out the immunization by an initial immunization with an amount of 100 µg/mouse, and a second and subsequent immunizations with an amount of 50 µg/mouse. In the immunization, an emulsion mixed with Complete Freund's adjuvant (CFA) was administered first, and for the second to fourth immunizations, an emulsion mixed with Incomplete Freund's adjuvant (IFA) was administered. The immunizations were carried out 4 times at 2-week interval. Separately, blood was collected the following week of the third and fourth immunizations, and antibody titers were measured by ELISA measurement using 100 µL of the collected serum. It was confirmed that the antibody titers were the target values, and the conjugate as an antigen was diluted and dissolved in 1 mL of a phosphate buffer solution (PBS, manufactured by Wako Pure Chemical Industries, Ltd., pH 7.1 to 7.3) and the resultant was intraperitoneally administered to a mouse, while taking the immunization two weeks after the fourth immunization as a final immunization. The spleen of the mouse was extracted 3 days after the administration.

Spleen cells extracted from the mouse and mutant myeloma cell lines (myeloma:P3-X63-Ag8-U1) were mixed at a ratio of 7:1 of the number of cells, and then polyethylene glycol (PEG) was added thereto. After centrifugation, the cells were suspended in a medium (RPMI-1640 (Roswell Park Memorial Institute Medium)+10% by mass fetal bovine serum (FBS)). The suspended spleen cells were seeded on a 96-well plate so that the number of cells was 1.0×10exp5 (cell/well). On the next day, HAT medium (hypoxanthine-aminopterin-thymidine medium) was added thereto and the culture supernatant of the grown hybridomas was screened by ELISA of the antibody assay system. The cholic acid-BSA conjugate, which is an antigen for measurement, was diluted with PBS to a concentration of 500 ng/mL, added to a cup of ELISA and left alone, and then immobilized at the bottom of the cup so as to remove the supernatant. An anti-mouse IgG HRP-labeled antibody was used as a secondary antibody against the antibody produced by the spleen cells of the measurement target. IgG shows immunoglobulin G and HRP shows horseradish peroxidase. Wells positive from the results of ELISA were cultured using a 24-well plate, and 1 mL of each culture supernatant was collected. Secondary screening was performed again by the same antibody assay system ELISA. In the same well at the time of cell fusion, the top 6 wells having high ELISA signals were selected and put in a vial.

The cells in each vial were subjected to limiting dilution using basal medium RPMI 1640 containing 10% by mass of FBS, and therefore dilutions were prepared. One drop of each dilution was pipetted and added into each well of six 96-well plates. Each well was observed under a microscope, and it was confirmed that the cells in each well were single cells. After culturing for 3 weeks, culture supernatants of the grown hybridomas were screened by ELISA of the antibody assay system in the same manner as described above. The top 10 wells with high ELISA signals were selected and hybridoma preparation was completed. An Isotyping kit (manufactured by Roche) was used to determine the subclass of the obtained antibody.

(3-3) Production of Antibody by Mouse Ascites Method

In the same manner, cells selected from the 10 wells were subjected to ELISA screening, and antibodies were produced by a mouse ascites method (using two mice) with respect to the top cells of the wells having a highest signal. The obtained antibody is referred to as an anti-cholic acid antibody-1.

(3-4) Preparation of Deoxycholic Acid Antibody and Chenodeoxycholic Acid Antibody The preparation of a deoxycholic acid antibody and a chenodeoxycholic acid antibody was carried out in the same manner as above. The obtained antibodies are referred to as an anti-deoxycholic acid antibody-1 and an anti-chenodeoxycholic acid antibody-1, respectively.

(3-5) Subclass of Antibody and Antibody Production

The subclass of the antibodies prepared above and an antibody production amount are shown in Table 2.

TABLE 2

Subclass and Antibody Production Amount

| Antibody | Subclass | Antibody production amount by mouse ascites method (2 mice) |
|---|---|---|
| Anti-cholic acid antibody-1 | IgG1 | 10.0 mg |
| Anti-deoxycholic acid antibody-1 | IgG1 | 28.7 mg |
| Anti-chenodeoxycholic acid antibody-1 | IgG1 | 30.4 mg |

(4) Production of Anti-Mouse Antibody

A mouse-derived globulin (LAMPIRE Biological Laboratories, Catalog No. 7404302, Mouse Gamma Globulin Salt Fractionation, 500 mg) was prepared, and the immunization of goats (subcutaneous immunization) was carried out four times at two-week intervals by using the method in which the emulsion mixed with Complete Freund's adjuvant (CFA) was administered first and for the second to fourth immunizations, the emulsion mixed with Incomplete Freund's adjuvant (IFA) was administered. Thereafter, ELISA measurement was carried out to confirm an increase in antibody titers, followed by performing of total blood collection, and antiserum was obtained by centrifugation. Thereafter, purification was carried out using Protein A column (Pierce Protein A Columns, catalog No. 20356, manufactured by Thermo scientific Co., Ltd.), and therefore a desired anti-mouse antibody was obtained.

(5) Production of Anti-CRP Antibody

Commercially available human CRP (manufactured by Kitayama Labes Co., Ltd.) was prepared, and the immunization of mice (subcutaneous immunization) was carried out four times at two-week intervals by using the method in which the emulsion mixed with Complete Freund's adjuvant (CFA) was administered first and for the second to fourth immunizations, the emulsion mixed with Incomplete Freund's adjuvant (IFA) was administered. Thereafter, ELISA measurement was carried out to confirm an increase in antibody titers, followed by performing of total blood collection, and antiserum was obtained by centrifugation. Thereafter, purification was carried out using Protein A column (Pierce Protein A Columns, catalog No. 20356, manufactured by Thermo scientific Co., Ltd.), and therefore a desired anti-CRP antibody-1 was obtained.

(6) Preparation of Fluorescent Particle 1 to which Three Types of Anti-Bile Acid Antibodies are Adsorbed Fluorescent particles labeled with three anti-bile acid antibodies were prepared as follows.

282 µL buffer solution (pH 6.0) with MES (2-morpholinoethanesulfonic acid) of 50 mmol/L was added to 357 µL aqueous solution with the fluorescent latex particles of 2% by mass (concentration of solid contents) (manufactured by Invitrogen, average particle size 200 nm), 5.3 µL with the anti-cholic acid antibody-1 of 5 mg/mL (produced above), 5.3 µL with the anti-deoxycholic acid antibody-1 of 5 mg/mL (produced above), 6.9 µL with the anti-chenodeoxycholic acid antibody-1 of 5 mg/mL (produced above), and 75.5 µL with the anti-CRP antibody-1 of 5 mg/mL (dummy) (produced above) were added thereto and stirred at room temperature for 15 minutes. Thereafter, 7.5 µL aqueous solution with EDC of 10 mg/mL was added thereto, and the mixture was stirred at room temperature for 1.5 hours. 37.5 µL aqueous solution with Glycine of 2 mol/L (manufacture by Wako Pure Chemical, Ltd.) was added thereto and stirred for 15 minutes, followed by centrifugation (15,000 rpm, 4°

C., 15 minutes) so as to precipitate fluorescent latex particles. rpm indicates revolution per minute, and 1 rpm=1 min. Thereafter, the supernatant was removed, 750 µL PBS (pH 7.4) was added, and fluorescent latex particles were redispersed with an ultrasonic washer. The centrifugation (15,000 rpm, 4° C., 15 minutes) was carried out again so as to remove the supernatant, then 750 µL PBS (pH 7.4) containing BSA of 1% by mass was added thereto so as to redisperse the fluorescent latex particles, and therefore a solution with the fluorescent latex particles of 1% by mass to which three types of the anti-bile acid antibodies and the anti-CRP antibody bound, was prepared.

(7) Production of Substrate

Polymethyl methacrylate (PMMA) substrate (ACRYPET (registered trademark) VH, manufactured by Mitsubishi Rayon Co., Ltd.) was prepared. By a magnetron sputtering method, a gold film with a thickness of 45 nm was produced on one side of two regions of a detection region and a reference region so that a width became 4 mm and a length became 3 mm, and was used as a chip constituting the substrate. A solution (concentration: 50 µg/mL in 50 mmol/L MES buffer solution, pH 6, 150 mmol/L NaCl) containing the conjugate 1, the conjugate 2, and the conjugate 3 by a content ratio (mass ratio 1:1:1) was spotted on the gold film surface of the detection region of the chip and dried, and therefore a plurality of substrates 1 on which the three types of the conjugates were immobilized were produced. In addition, the solution (concentration: 50 µg/mL in 50 mmol/L MES buffer solution, pH 6, 150 mmol/L NaCl) containing the anti-mouse antibody produced in (4) was spotted on the reference region of each substrate and dried.

Before using the plurality of substrates 1 prepared as above as a flow passage of the sensor chip, the substrates were repeatedly washed 3 times using 300 µL of a cleaning solution prepared in advance (PBS (pH 7.4) containing TWEEN 20 (POLYOXYETHYLENE (20) SORBITAN MONOLAURATE manufactured by Wako Pure Chemical, Ltd.) of 0.05% by mass).

(8) Production of Flow Passage-Type Sensor Chip

Figure 2:
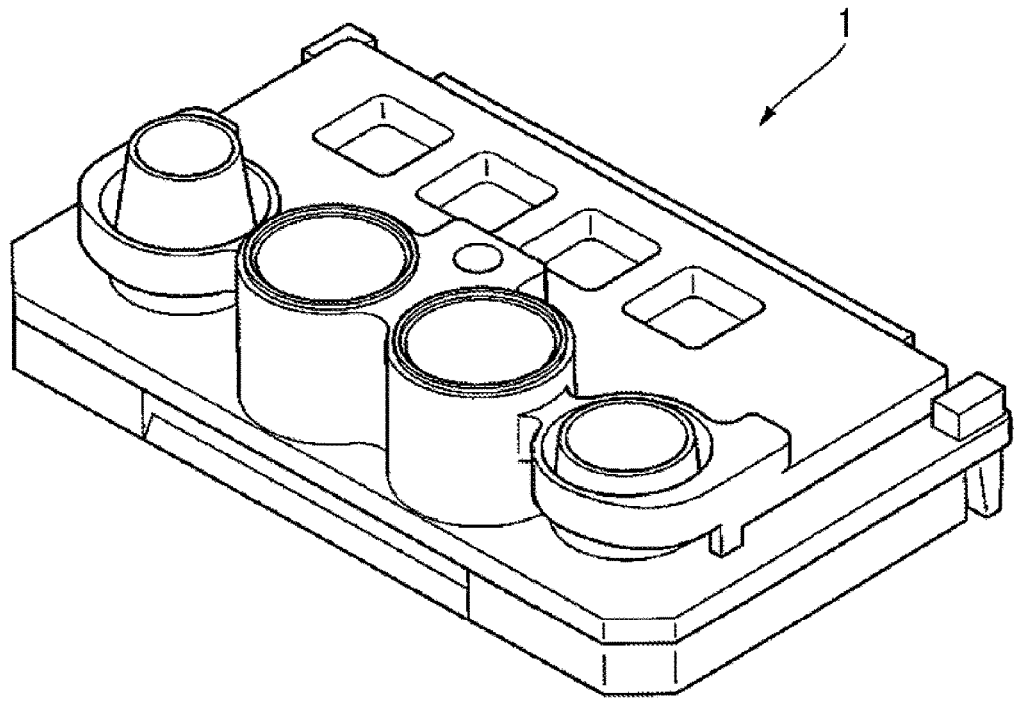
FIG. 2 shows a schematic view of a sensor chip provided in a kit of the present invention.
Figure 3:
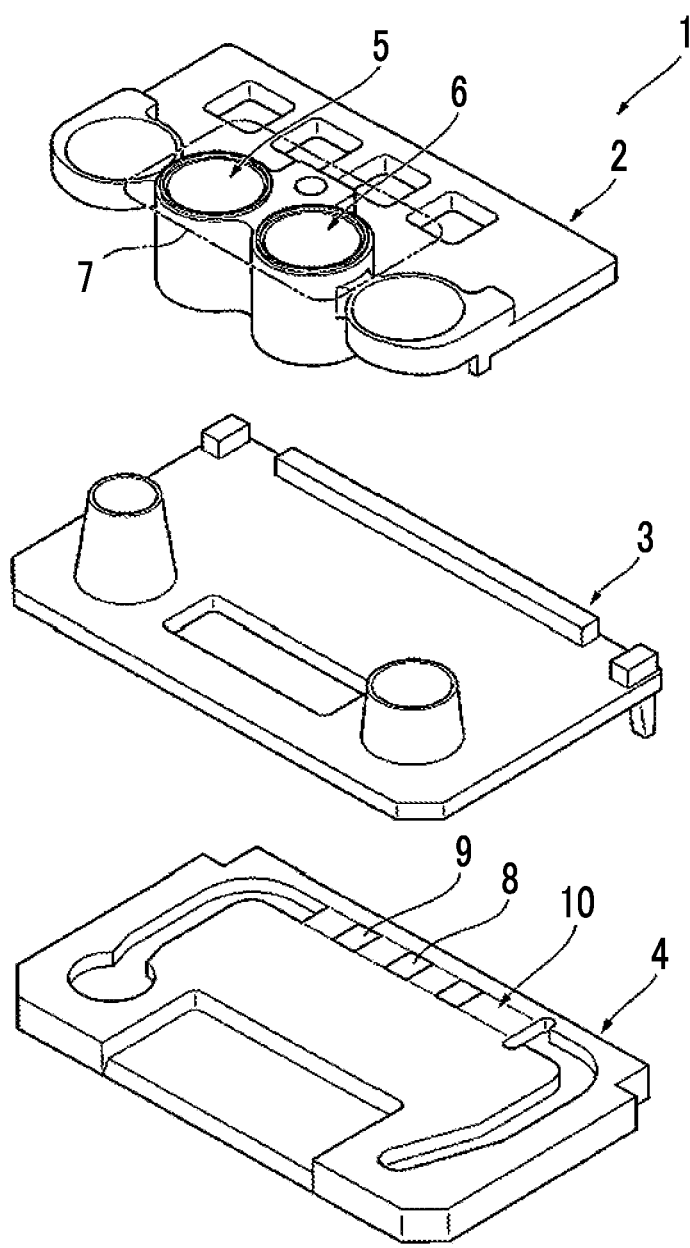
FIG. 3 shows an exploded view of the sensor chip provided in the kit of the present invention.

A flow passage-type sensor chip was produced so as to have the configuration of the second embodiment of JP2010-190880A. FIGS. 2 and 3 are schematic views of the sensor chip. FIG. 2 is the schematic view of a sensor chip 1, and FIG. 3 is an exploded view of the sensor chip 1. The sensor chip 1 is configured of an upper member 2, an intermediate member 3, and a substrate 4. The upper member 2 has a first container 5 and a second container 6. The first container 5 and the second container 6 are collectively referred to as a container group 7. A flow passage 10 is formed in the substrate 4, and a detection region 8 and a reference region 9 are formed on the flow passage 10.

(9) Measurement with Large Machine (Existing Bile Acid Measurement Reagent) By immunoassay, 76 types of samples with different amounts of bile acids were prepared and each was measured by using HITACHI 7170 AUTOMATIC ANALYZER, which is a large machine widely used by those skilled in the art, according to an instruction manual so as to obtain measurement amounts of bile acids, and therefore a sample having a known amount of bile acids was prepared.

(10) Immunoassay of Bile Acids Using Fluorescent Particles (10-1) Immunoassay of Bile Acid in Case of Using Dissociator of Compound 1

A dedicated cup was prepared, and 51 µg of a dissociator of compound 1 was added thereto and dried. A sample having the known amount of bile acids measured by the large machine of (9) (HITACHI 7170 AUTOMATIC ANALYZER) was prepared. 100 µL of the above sample was added to the cup containing the compound 1 (moisture content of 15% by mass or less) dried under the environment of 25° C., and the dissociator and the sample were dissolved and mixed and left alone for 5 minutes. Thereafter, the mixture was mixed in advance in a cup containing fluorescent particles 1 to which the three types of the bile acid antibodies prepared in (6) had been adsorbed, while stirring for 10 minutes. Next, the resultant was spotted on the each flow passage-type sensor chip in which the substrate 1 produced in (7) was installed. After spotting, the mixed solution was allowed to flow down at a rate of 10 µL/min while performing pump suction and brought into contact with the gold film surface to which the bile acid-BSA conjugate was immobilized, and then surface plasmon was continuously generated on the detection region and the reference region for 1.5 minutes so as to measure the intensity of the emitted fluorescence. The increase rate of fluorescence intensity in unit time of each of the detection region and the reference region obtained in each substrate was obtained as a change rate of a fluorescence signal value, and a change rate of a signal value of the detection region was divided by a change rate of a signal value of the reference region so as to carry out the standardization. In addition, a sample with a concentration of bile acids of 0 was prepared, and a fluorescence signal value was standardized from the sample not containing the bile acids in the same manner.

(10-2) Immunoassay of Bile Acid in Case of Using Salicylic Acid as Dissociator Immunoassay was carried out and a fluorescence signal value was standardized in the same manner as (10-1), except that the dissociator of compound 1 was changed to a salicylic acid (1.12 mg per dedicated cup) in the immunoassay of (10-1).

(11) Creation of Calibration Curve

The fluorescence signal values standardized for the sample having the known amount of bile acids, which were obtained in (10-1) and (10-2), was allowed to correspond to the measurement value of the same sample obtained by the large machine in (9), and therefore a calibration curve was created for each measurement using the compound 1 or the salicylic acid as the dissociator.

(12) Confirmation of Improvement in Correlation with Existing Bile Acid Reagent

In the same manner as the immunoassay described in (10-1) and (10-2), the dissociation of the bile acids from proteins was carried out with respect to each of 76 samples of commercially available dog samples, by using the compound 1 or the salicylic acid as the dissociator. In all the 76 samples, an amount of bile acids was determined from the calibration curve and plotted with respect to the value obtained by the control method using the large machine, and therefore a correlation coefficient was obtained. The results are shown in FIG. 1.

In FIG. 1, y=0.97x+0.03 and y=0.98x+0.09 indicate correlation equations, respectively, and R represents a correlation coefficient.

Based on the results shown in FIG. 1, it was found that the correlation was improved by using the compound 1 as the dissociator of the present invention as compared with the salicylic acid, and the effects of the present invention were confirmed.

Example 2

In (12) of Example 1, measurement results were obtained for the 76 samples under the environment of 5° C. using a dissociator 1. As a result of plotting the result against the value acquired under the environment of 25° C. by the control method using the large machine, an accurate correlation coefficient, which was as favorable as in the results measured under the environment of 25° C., was obtained, and it was confirmed that measurements not affected by the environment can be realized.

Example 3

In (12) of Example 1, even in a case where a compound 2 in a dry state (moisture content of 15% by mass or less) was used as a dissociator, a correlation coefficient of R=0.94, which was equivalent to that in the case of the compound 1, was obtained, and therefore the effects of the present invention were confirmed.

Comparative Example 1

In a case where a dissociator in which the countercation of the compound 1 which is a dissociator was changed to $Mg^{2+}$, was used, the solubility in dog serum was low, leading to a high level of the dissolution with respect to the measurement result using the large machine, and therefore the measurement could not be carried out.

EXPLANATION OF REFERENCES

1: sensor chip
2: upper member
3: intermediate member
4: substrate
5: first container
6: second container
7: container group
8: detection region
9: reference region
10: flow passage

What is claimed is:
1. A kit for quantitatively determining a bile acid in a biological sample, comprising:
a compound represented by General Formula (I) in a dry state;
a fluorescent particle that has a first binding substance capable of binding to the bile acid; and
a substrate that has a detection region having a second binding substance capable of binding to any one of the bile acid and the first binding substance, wherein a metal film is disposed on the substrate,

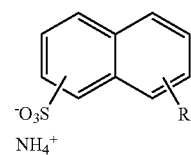

General Formula (I)

in the formula, R represents —NH—$C_6H_5$, —$NH_2$, or —NH—$CH_2$—$CH_2$—$NH_2$.

2. The kit according to claim 1,
wherein in General Formula (I), a group represented by R is present at a 5-position, a 7-position, or an 8-position of a naphthalene ring, provided that substitution positions in the naphthalene ring are as follows

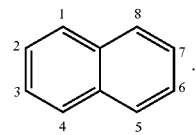

3. The kit according to claim 1,
wherein in General Formula (I), R represents —NH—$C_6H_5$.

4. The kit according to claim 1,
wherein in General Formula (I), a group represented by —$SO_3^-$ is present at a 1-position or a 3-position of a naphthalene ring, provided that substitution positions in the naphthalene ring are as follows

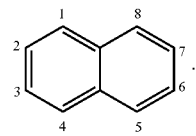

5. The kit according to claim 1,
wherein the substrate further has a reference region in which measurement for correcting data obtained in the detection region is performed.

6. The kit according to claim 1,
wherein the fluorescent particle that has the first binding substance capable of binding to the bile acid is a fluorescent colloidal particle having the first binding substance capable of binding to the bile acid.

7. The kit according to claim 6,
wherein the fluorescent particle is a fluorescent latex particle.

8. The kit according to claim 1,
wherein the first binding substance capable of binding to the bile acid is at least three types of antibodies capable of binding to the bile acid.

9. The kit according to claim 8,
wherein the at least three types of antibodies capable of binding to the bile acid include an anti-cholic acid antibody, an anti-deoxycholic acid antibody, and an anti-chenodeoxycholic acid antibody.

10. A method for quantitatively determining a bile acid in a biological sample with the kit according to claim 1, the method comprising:
a treatment step of treating a biological sample with the compound represented by General Formula (I) in a dry state;
a reaction step of reacting the biological sample treated in the treatment step with the fluorescent particle having the first binding substance capable of binding to the bile acid; and
a biological sample-related fluorescence information acquisition step of acquiring fluorescence information related to an amount of the biological sample,
wherein the fluorescence information is acquired via the substrate having the metal film disposed thereon,
wherein the substrate has the detection region having the second binding substance capable of binding to any one of the bile acid and the first binding substance, General Formula (I)

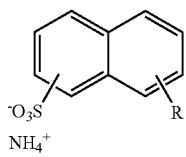

in the formula, R represents —NH—$C_6H_5$, —$NH_2$, or —NH—$CH_2$—$CH_2$—$NH_2$.

11. The method according to claim 10, wherein in General Formula (I), a group represented by R is present at a 5-position, a 7-position, or an 8-position of a naphthalene ring, provided that substitution positions in the naphthalene ring are as follows

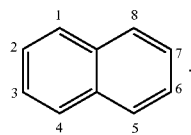

12. The method according to claim 10, wherein in General Formula (I), R represents —NH—$C_6H_5$.

13. The method according to claim 10, wherein in General Formula (I), a group represented by —$SO_3^-$ is present at a 1-position or a 3-position of a naphthalene ring, provided that substitution positions in the naphthalene ring are as follows

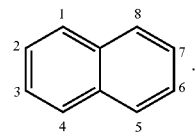

14. The method according to claim 10, further comprising:
a fluorescent particle-related fluorescence information acquisition step of acquiring fluorescence information related to an amount of the fluorescent particle; and
a standardization step of standardizing the fluorescence information acquired in the biological sample-related fluorescence information acquisition step by the fluorescence information acquired in the fluorescent particle-related fluorescence information acquisition step.

15. The method according to claim 10, wherein the fluorescent particle that has the first binding substance capable of binding to the bile acid is a fluorescent colloidal particle having the first binding substance capable of binding to the bile acid.

16. The method according to claim 15, wherein the fluorescent particle is a fluorescent latex particle.

17. The method according to claim 10, wherein the first binding substance capable of binding to the bile acid is at least three types of antibodies capable of binding to the bile acid.

18. The method according to claim 17, wherein the at least three types of antibodies capable of binding to the bile acid include an anti-cholic acid antibody, an anti-deoxycholic acid antibody, and an anti-chenodeoxycholic acid antibody.

* * * * *